United States Patent [19]

Teng et al.

[11] 4,364,856
[45] Dec. 21, 1982

[54] MIXED METAL PHOSPHORUS OXIDE COATED CATALYSTS FOR THE OXIDATIVE DEHYDROGENATION OF CARBOXYLIC ACIDS

[75] Inventors: Harry H. I. Teng, Waldwick, N.J.; S. Erik Pedersen, Mentor, Ohio

[73] Assignee: The Standard Oil Company, Cleveland, Ohio

[21] Appl. No.: 225,572

[22] Filed: Jan. 16, 1981

[51] Int. Cl.$^3$ .......................... B01J 27/14; B01J 21/02
[52] U.S. Cl. ...................................... 252/437; 252/432
[58] Field of Search ............................... 252/432, 437

[56] References Cited

U.S. PATENT DOCUMENTS

| | | | |
|---|---|---|---|
| 3,207,806 | 9/1965 | Bajars | 260/680 |
| 3,308,193 | 3/1967 | Bajars | 260/680 |
| 3,398,100 | 8/1968 | Christmann | 252/435 |
| 3,530,169 | 9/1970 | Platz et al. | 260/486 |
| 3,634,494 | 1/1972 | Tsu | 260/486 D |
| 3,652,654 | 3/1972 | Tsu | 260/486 D |
| 3,716,545 | 2/1973 | Ripley | 260/290 V |
| 3,855,279 | 12/1974 | Watkins | 260/486 D |
| 3,862,910 | 1/1975 | Cichowski | 252/435 |
| 3,870,764 | 3/1975 | Cichowski et al. | 252/437 X |
| 3,917,673 | 11/1975 | Watkins | 260/486 D |
| 3,928,389 | 12/1975 | Farha, Jr. et al. | 252/437 X |
| 3,948,959 | 4/1976 | Cavaterra et al. | 260/405.5 |
| 3,956,377 | 5/1976 | Dolhyj et al. | 260/530 N |
| 3,960,767 | 6/1976 | Christmann et al. | 252/437 |
| 3,993,591 | 11/1976 | Cichowski et al. | 252/432 |
| 4,010,114 | 3/1977 | Walker et al. | 252/437 |
| 4,026,820 | 5/1977 | Farha, Jr. et al. | 252/432 |
| 4,029,695 | 6/1977 | Watkins | 260/486 D |
| 4,077,912 | 3/1978 | Dolhyj et al. | 252/461 |
| 4,094,819 | 6/1978 | Bertus | 252/435 |
| 4,110,369 | 8/1978 | White et al. | 260/330 N |
| 4,155,920 | 5/1979 | Milberger et al. | 260/346.75 |
| 4,251,393 | 2/1981 | Dalton et al. | 252/443 |
| 4,276,196 | 6/1981 | Dalton et al. | 252/435 |

*Primary Examiner*—Delbert E. Gantz
*Assistant Examiner*—William G. Wright
*Attorney, Agent, or Firm*—Joseph G. Curatolo; Herbert D. Knudsen; Larry W. Evans

[57] ABSTRACT

A process is provided for the preparation of coated iron phosphorus oxide containing catalysts useful in the oxydehydrogenation of saturated carboxylic acids, wherein the catalysts are prepared by partially wetting a carrier or support in an aqueous silica solution/suspension, contacting the partially wet carrier with a powder of the iron phosphorus oxide catalyst, drying and calcining.

19 Claims, No Drawings

MIXED METAL PHOSPHORUS OXIDE COATED CATALYSTS FOR THE OXIDATIVE DEHYDROGENATION OF CARBOXYLIC ACIDS

BACKGROUND OF THE INVENTION

This invention relates to the catalytic, oxidative dehydrogenation of saturated carboxylic acids to their corresponding unsaturated acids. More particularly, it is directed to the production of unsaturated carboxylic acids such as methacrylic acid from saturated carboxylic acids such as isobutyric acid utilizing coated iron phosphorus oxide catalysts.

The production of unsaturated carboxylic acids from their corresponding saturated acids using iron phosphorus oxide catalysts, with or without various promoters, is disclosed in the art.

U.S. Pat. No. 3,948,959 discloses the preparation of unsaturated acids by oxidation of the corresponding saturated acid using iron phosphorus oxide catalysts promoted with Li, Na, K, Rb, Cs, Mg, Ca, Sr and Ba. U.S. Pat. Nos. 3,634,494; 3,652,654; 3,855,279; 3,917,673 and and 4,029,695 disclose the preparation of unsaturated acids and esters from saturated acids and esters using iron phosphorus oxide catalysts, containing bismuth and/or lead promoters, optionally with other promoter elements, including Mn, U, Pr, Ca, Sr, and Cr. Prior art catalysts characteristically have exhibited short life and thermal instability.

Coated catalysts useful for exothermic reactions and a method of coating such catalysts are disclosed in U.S. Pat. No 4,077,912. Coated catalysts comprising the oxides of molybdenum, phosphorus, arsenic, and copper, useful for the production of methacrylic acid from methacrolein, are disclosed in U.S. Pat. No. 4,110,369.

These prior art coated catalysts are prepared by contacting an inert support with a liquid, preferably water, to produce a partially wet support and rolling the partially wet support in a powder of the catalytic material.

Coated catalysts, prepared by the above technique with either water or ethanol as the liquid wetting agent, are disclosed in copending patent application U.S. Ser. No. 221,859 by S. E. Pedersen, J. L. Callahan and H. F. Hardman directed to Mixed Metal Phosphorus Oxide Catalysts for the Oxidative Dehydrogenation of Carboxylic Acids, and assigned to our common assignee.

It is an object of the present invention to provide coated catalysts useful for the oxydehydrogenation of saturated carboxylic acids, which coated catalysts exhibit improved activity and attrition resistance.

It is a further object of the present invention to provide a process for the production of unsaturated acids from their corresponding saturated acids.

SUMMARY OF THE INVENTION

We have found that iron phosphorus oxide catalysts, when coated according to the method set forth below, using an aqueous solution or colloidal suspension of silica containing liquid as a wetting or binding agent, results in the improvement of catalyst attrition resistance and physical integrity, as well as an increase of catalyst activity over such catalysts coated according to the prior art.

In general, the present invention includes the preparation of catalysts containing the mixed oxides of iron and phosphorus coated upon a carrier by partially wetting the carrier with a liquid which comprises an aqueous solution or colloidal suspension of silica by contacting the carrier with the liquid such that at least some liquid is absorbed by the carrier, contacting the partially wet carrier with a powder of the iron phosphorus oxide to form a mixture, agitating the mixture to form the coated catalyst, and drying the coated catalyst.

The present invention includes the preparation of unsaturated acids by contacting their corresponding saturated acids with molecular oxygen or an oxygen-containing gas in the vapor phase, at a reaction temperature of about 250° C. to about 600° C. in the presence of a catalyst containing iron phosphorus oxides coated on a carrier prepared by wetting the carrier surface with a liquid which comprises an aqueous solution or colloidal suspension of silica by contacting the carrier with the liquid such that at least some liquid is absorbed by the carrier, contacting the partially wet carrier with a powder of the iron phosphorus oxide to form a mixture, agitating the mixture to form the coated catalyst and drying the coated catalyst.

DETAILED DESCRIPTION OF THE INVENTION

Saturated carboxylic acids are oxidatively dehydrogenated according to the process of the present invention in the vapor phase, in the presence of promoted iron phosphorus oxide catalysts to form the corresponding unsaturated acid. The saturated acids preferably correspond to the formula

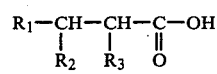

wherein $R_1$, $R_2$, and $R_3$ are each independently selected from the group consisting of hydrogen and alkyl groups containing 1 to 4 carbon atoms. The acids may contain other functional groups such as aryl or nitrile, provided the functional groups do not interfere with the dehydrogenation reaction under the reaction conditions required. The dehydrogenation occurs essentially in the alpha, beta position.

The process of the present invention is highly suitable for the oxidative dehydrogenation of isobutyric acid to methacrylic acid.

Iron phosphorus oxide catalysts may be coated according to the procedure set forth above, using as the wetting liquid, an aqueous solution or colloidal suspension of silica ($SiO_2$). Preferred are promoted iron phosphorus catalysts have the empirical formula

wherein
  A is selected from the group Al, B, Be, Cd, Co, Cr, Ga, Ge, In, Ni, Te, Th, Ti, Tl, U, V, Zn, Zr, rare earths and mixtures thereof,
wherein
  D is selected from the group Ag, Cu, Mn and mixtures thereof,
and wherein
  a=0–1.0
  b=0.75–1.5
  c=1.0–2.0
  d=0–2.0
  a+d is greater than zero and
  x is the number of oxygens needed to satisfy the valence requirements of the remaining elements.

Preferably a equals 0.15–0.5 and d equals 0.2–1.5. Most preferred are catalysts of the empirical formula $$A_aFe_bP_cD_dO_x$$

wherein
A is selected from the group Cd, Cr, Ge, Te, Th, Ti, U, V, Zr, rare earths and mixtures thereof;
wherein
D is selected from the group Ag, Cu, Mn and mixtures thereof,
and wherein
a=0–1.0
b=0.75–1.5
c=1.0–2.0
d=0–2.0
a+d is greater than zero and
x is the number of oxygens needed to satisfy the valence requirements of the remaining elements.

Preferably a equals 0.15–0.5 and d equals 0.2–1.5. Preferred rare earth metal promoters are La, Ce, Nd, Sm, Eu, Dy, Ho, Tm, Yb and Lu.

The catalyst oxide powder may be prepared according to methods known in the art.

One method of preparing the catalyst oxide powder includes introducing a compound of iron and a compound containing the promoter element, if any, into water and contacting with a phosphorus compound, or the iron and promoter containing compound are introduced into an aqueous solution of phosphoric acid. Preferably, the compounds used containing iron and the promoter elements are soluble in water, and may include salts such as nitrates, halides, sulfates, acetates, carbonates, formates and the like. The resulting solution or slurry is evaporated to dryness, and the resulting solid may be calcined at from about 300° to 700° C. Alternatively, the catalyst may be prepared in an organic liquid medium. Alternatively, the aqueous solution or slurry can be adjusted to a pH of about 5–6 before drying.

The resulting iron phosphorus oxide catalyst may be ground to form the oxide powder which is used in the preparation of the coated catalyst. The catalyst may additionally be combined with inert diluents.

When the catalyst is prepared according to the technique of the present invention, the carrier or support material for the catalyst forms the inner core of the catalyst. This is preferably an essentially inert support and may have substantially any particle size although a diameter of at least 20 microns is preferred. Especially preferred in the present invention for use in a commercial reactor are those supports which are spherical and which have a diameter of about 0.2 cm. to about 2 cm.

In the preferred procedure of the invention, the support material employed is at least partially porous. By this is meant the support material must be susceptible to the penetration of liquid. Preferred support materials are capable of absorbing at least about 1% by weight of water based upon the weight of the support. Suitable examples of essentially inert support materials include: Alundum (Norton Company), silica, alumina, alumina-silica, silicon carbide, titania and zirconia. Especially preferred among these supports are Alundum, silica, alumina and alumina-silica.

The catalysts may contain essentially any portions of support and catalytically active material. Preferred catalysts contain about 5 to about 50 percent by weight of catalytically active material based on the total weight of the support and active material.

The total coated catalyst of the present invention is conveniently prepared by partially wetting the inert support with a liquid which comprises silica ($SiO_2$) in water, such as in an aqueous soution or colloidal suspension of silica. The colloidal suspension may be acid or base stabilized. The liquid may contain about 5–60% silica by weight, and preferably contains about 10–30% silica by weight.

The partially wet support should contain some liquid, but there should be no surface liquid visible. The partially wet support is contacted with a powder of the active ingredient composition, and the inert support is rolled or agitated in the active ingredients. In one embodiment of the invention, the contact between the powder and inert support is easily accomplished by placing the support in a closed container, rotating the container in an inclined plane and adding portions of the powder. Preferably, substantially all of one portion of the powder is coated on the support before another portion is added.

The coated catalyst is dried and then calcined at from about 300° C. to 700° C. The final coated catalyst thus prepared generally contains about 1% to 10% $SiO_2$ by weight. The coated iron phosphorus oxide containing catalyst prepared according to the process of the present invention exhibits excellent physical integrity, high attrition resistance, and enhanced activity and selectivity for the oxydehydrogenation of saturated carboxylic acids, particularly isobutyric acid, compared with coated catalysts prepared with water alone as the wetting agent.

The saturated acids are contacted with the catalyst in the vapor phase, together with molecular oxygen. The molecular oxygen is most conveniently added as air, but synthetic streams containing oxygen are also suitable. In addition to the carboxylic acid feed and molecular oxygen, other gases may be added to the reactant feed. For example, steam is preferably added to the reactant feed to aid in the reaction, although the mechanism by which it does so is not certain. Inert diluents such as nitrogen, carbon monoxide, carbon dioxide and argon may also be added.

The molar ratio of the reactants may vary widely and are not critical. The ratios of carboxylic acid:air:steam are in the range of 1:2.5–50:0–50 and are preferably 1:3–10:10–30. Diluents may be present in the range of 0–40 moles per mole of carboxylic acid.

The reaction temperature may vary widely and is dependent upon the particular carboxylic acid and catalyst employed. Normally, temperatures of about 250° to 600° C. are employed with temperatures of 325°–450° C. being preferred.

The contact time may vary from a fraction of a second to about 50 seconds. In fixed bed reactions the contact time is preferably about 0.5 seconds to about 10 seconds, and for fluid bed, preferably from about 2 seconds to about 20 seconds. The reaction may be conducted at atmospheric, superatmospheric or subatmospheric pressure, preferably from about 1 psia to about 100 psia, most preferably between about 10 to about 30 psia.

In the production of methacrylic acid from isobutyric acid, the major by-product is acetone (generally about 5–15% yield) which may be removed from the product by conventional methods.

SPECIFIC EMBODIMENTS OF THE INVENTION

Coated catalysts tested in the below examples were prepared according to the following procedure.

$Fe(NO_3)_3.9H_2O$, the appropriate promoter metal nitrate and $H_3PO_4$ (85%) were added to water in the amounts necessary to provide the molar ratios set forth in the tables below, for each of the particular catalysts reported. The solution of the components was evaporated to a dry paste with heating and stirring. The paste was dried for about 16 hours at 110° C., and the resulting solid was calcined for about 2 hours at 540° C. The solid was crushed and ground to a fine powder to pass through about 50 mesh (0.3 mm).

EXAMPLES 1-4

20 grams of ⅛" (0.31 cm) Norton SA 5209 Alundum carrier was partially wetted with 4.5 g Nalco silica sol (10 weight % silica in water). The partially wetted carrier was contacted and agitated with 10.8 grams of catalyst oxide, which oxide had been powdered (to pass 50 mesh), having the empirical formula $Ag_{0.8}Fe_{1.2}P_{1.84}O_x$ and which catalyst oxide had been calcined for 2 hours at 540° C. The resulting coated catalyst had a firm, hard coating of active material, about 35% by weight, and contained about 1.5% by weight $SiO_2$.

COMPARATIVE EXAMPLES 5-7

The procedure of examples 1-4 was repeated, except that water alone was used as the wetting liquid.

EXAMPLES 8-10

Coated catalysts of the formula 45% $Ag_{0.8}Fe_{1.2}P_{1.84}O_x$/55% Alundum were prepared according to the procedure of examples 1-4.

EXAMPLES 11-12

Coated catalysts of the formula 45% $Ag_{0.8}Fe_{1.0}P_{1.84}O_x$/55% Alundum were prepared according to the procedure of examples 1-4.

EXAMPLES 13-14

Coated catalysts of the formula 35% $Ag_{0.8}Fe_{1.0}P_{1.84}O_x$/65% Alundum were prepared according to the procedure of examples 1-4.

EXAMPLES 15-17

Coated catalysts of the formula 35% $Mn_{0.5}Fe_{1.0}P_{1.84}O_x$/65% Alundum were prepared according to the procedure of examples 1-4.

COMPARATIVE EXAMPLES 18-20

Coated catalysts of the formula 35% $Mn_{0.5}Fe_{1.0}P_{1.84}O_x$/65% Alundum were prepared as in examples 15-17, except that water alone was used as the wetting liquid.

The coated catalysts prepared in the above examples were tested for the oxydehydrogenation of isobutyric acid to methacrylic acid in a 20 cc fixed bed reactor. The reactor consisted of a length of stainless steel tubing having an outer diameter of about 1.3 cm, and containing a full length 0.31 cm diameter axial thermowell. The reactor was heated with a split stainless steel block furnace.

The isobutyric acid was fed to the reactor by passing air through a saturator filled with isobutyric acid and maintained at a temperature of 108° C. Water was fed by means of a tubing pump and vaporized in a compartment maintained at about 154° C. before entering the reactor. Liquid products were analyzed on a Hewlett Packard 5710A F.I.D. gas chromatograph. Gaseous products were analyzed on a conventional split column system.

The test reactions were run at atmospheric pressure. Reaction conditions such as temperature, feed ratios, contact time and catalyst working rate (WWH=weight of isobutyric acid/weight of catalyst/hour) are listed in the Table below. Results of the tests reported in the Table below are reported in terms as follows:

$$\text{Single Pass Yield} = \frac{\text{Moles of Methacrylic Acid Formed} \times 100}{\text{Moles of Isobutyric Acid Fed}}$$

$$\text{Total Conversion} = \frac{\text{Moles of Isobutyric Acid Reacted} \times 100}{\text{Moles of Isobutyric Acid Fed}}$$

$$\text{Selectivity} = \frac{\text{Single Pass Yield} \times 100}{\text{Total Conversion}}$$

As is demonstrated by the test results reported in the Table, coated iron phosphorus oxide catalysts according to the present invention exhibit high activity and selectivity in the oxydehydrogenation of saturated carboxylic acids, particularly isobutyric acid, to the corresponding unsaturated acid. The coated catalysts of the invention additionally exhibit improved attrition resistance and physical integrity compared to coated catalysts prepared according to the prior art.

Thus it should be apparent to those skilled in the art that the subject invention accomplishes the objects set forth above. It is to be understood that the subject invention is not to be limited by the examples set forth herein. These have been provided merely to demonstrate operability, and the selection of iron and phosphorus-containing compounds, promoter element-containing compounds, support or carrier materials, preparation techniques, reaction feedstocks and reaction conditions can be determined from the total specification disclosure provided without departing from the spirit of the invention herein disclosed and described, the scope of the invention including modifications and variations that fall within the scope of the attached claims.

TABLE

OXYDEHYDROGENATION OF ISOBUTYRIC ACID TO METHACRYLIC ACID OVER COATED IRON PHOSPHORUS OXIDE CATALYSTS

| Example No. | % Active Coating | Feed Ratio IBA/Air/$H_2O$ | Temperature °C. | Contact Time (sec.) | WWH | Methacrylic Acid % Yield | % Selectivity | % Conversion | Hours On Stream |
|---|---|---|---|---|---|---|---|---|---|
| $Ag_{0.8}Fe_{1.2}P_{1.84}O_x$ | | | | | | | | | |
| 1 | 35 | 1/4.9/25.3 | 406 | 0.9 | 0.19 | 73.2 | 74.6 | 98.2 | 18 |
| 2 | 35 | 1/4.9/25.3 | 406 | 0.9 | 0.19 | 73.5 | 75.5 | 97.4 | 25 |
| 3 | 35 | 1/4.9/32.1 | 403 | 0.7 | 0.19 | 75.1 | 76.7 | 97.9 | 48 |
| 4 | 35 | 1/5.0.37.3 | 403 | 0.6 | 0.19 | 73.8 | 76.0 | 97.1 | 72 |
| C 5 | 35 | 1/4.9/25.3 | 453 | 0.8 | 0.18 | 51.5 | 52.7 | 97.8 | 2 |

TABLE-continued

OXYDEHYDROGENATION OF ISOBUTYRIC ACID TO METHACRYLIC ACID OVER COATED IRON PHOSPHORUS OXIDE CATALYSTS

| Example No. | % Active Coating | Feed Ratio IBA/Air/H$_2$O | Temperature °C. | Contact Time (sec.) | WWH | Methacrylic Acid % Yield | % Selectivity | % Conversion | Hours On Stream |
|---|---|---|---|---|---|---|---|---|---|
| C 6 | 35 | 1/4.9/25.3 | 452 | 0.9 | 0.18 | 49.6 | 50.9 | 97.4 | 9 |
| C 7 | 35 | 1/4.9/25.3 | 454 | 0.9 | 0.18 | 41.2 | 45.8 | 90.0 | 27 |
| 8 | 45 | 1/4.9/26.1 | 410 | 0.8 | 0.18 | 70.4 | 71.2 | 98.8 | 1 |
| 9 | 45 | 1/4.9/26.1 | 394 | 0.9 | 0.18 | 70.5 | 73.7 | 95.6 | 25 |
| 10 | 45 | 1/4.9/26.2 | 415 | 0.8 | 0.18 | 64.8 | 68.7 | 94.3 | 33 |
| Ag$_{0.8}$Fe$_{1.0}$P$_{1.84}$O$_x$ | | | | | | | | | |
| 11 | 45 | 1/4.4/33.2 | 436 | 0.7 | 0.17 | 74.0 | 77.5 | 95.5 | 3 |
| 12 | 45 | 1/3.2/33.2 | 436 | 0.7 | 0.17 | 68.2 | 79.4 | 86.0 | 27 |
| 13 | 35 | 1/5.1/26.2 | 442 | 0.8 | 0.18 | 74.2 | 76.1 | 97.6 | 6 |
| 14 | 35 | 1/3.5/33.2 | 447 | 0.7 | 0.18 | 74.1 | 77.2 | 96.0 | 16 |
| Mn$_{0.5}$Fe$_{1.0}$P$_{1.84}$O$_x$ | | | | | | | | | |
| 15 | 35 | 1/5.1/25.3 | 403 | 0.9 | 0.28 | 70.4 | 72.0 | 97.8 | 7 |
| 16 | 35 | 1/4.3/25.3 | 404 | 0.9 | 0.28 | 73.0 | 76.2 | 95.7 | 26 |
| 17 | 35 | 1/4.3/25.3 | 409 | 0.9 | 0.28 | 70.8 | 73.6 | 96.2 | 29 |
| C 18 | 35 | 1/5.0/25.9 | 409 | 0.9 | 0.21 | 69.5 | 72.2 | 96.2 | 23 |
| C 19 | 35 | 1/4.7/25.3 | 421 | 0.9 | 0.21 | 66.8 | 67.7 | 98.7 | 48 |
| C 20 | 35 | 1/4.7/32.4 | 414 | 0.7 | 0.21 | 68.8 | 71.5 | 96.2 | 52 |

We claim:

1. A process for the preparation of coated iron phosphorus oxide containing catalysts comprising
   (a) partially wetting a carrier with a liquid comprising a solution or colloidal suspension of SiO$_2$ in water;
   (b) contacting the partially wet carrier with a powder of the iron phosphorus oxide catalyst to form a mixture;
   (c) agitating said mixture to form the coated catalyst;
   (d) drying said coated catalyst;
   (e) calcining said coated catalyst.

2. A process as in claim 1, wherein said carrier is an essentially inert support.

3. A process as in claim 1, wherein said carrier is selected from the group silica, alumina, alumina-silica, silicon carbide, titania and zirconia.

4. A process as in claim 1, wherein said liquid contains about 5% to about 60% silica by weight.

5. A process as in claim 1, wherein said liquid contains about 10 to about 30% silica by weight.

6. A process as in claim 1, wherein said coated catalyst contains up to 10% silica by weight.

7. A process as in claim 1, wherein said iron phosphorus oxide catalyst has the empirical formula $$A_aFe_bP_cD_dO_x$$

wherein
A is selected from the group Al, B, Be, Cd, Co, Cr, Ga, Ge, In, Ni, Te, Th, Ti, Tl, U, V, Zn, Zr, rare earths and mixtures thereof,
wherein
D is selected from the group Ag, Cu, Mn and mixtures thereof,
and wherein
a=0-1.0
b=0.75-1.5
c=1.0-2.0
d=0-2.0
a+d is greater than zero and
x is the number of oxygens needed to satisfy the valence requirements of the remaining elements.

8. A process as in claim 7, wherein a is about 0.15 to about 0.5.

9. A process as in claim 7, wherein d is about 0.2 to about 1.5.

10. A process as in claim 7 wherein said rare earths are selected from the group consisting of La, Ce, Nd, Sm, Eu, Dy, Ho, Tm, Yb, Lu and mixtures thereof.

11. A process as in claim 7, wherein said catalyst contains silver.

12. A process as in claim 7, wherein said catalyst contains copper.

13. A process as in claim 7, wherein said catalyst contains manganese.

14. A process as in claim 7, wherein said catalyst contains thorium.

15. A process as in claim 7, wherein said catalyst contains uranium.

16. A process as in claim 1, wherein said catalyst additionally contains inert diluents.

17. An iron phosphorus oxide catalyst coated upon a carrier, prepared by
   (a) partially wetting the carrier with a liquid comprising a solution or colloidal suspension of SiO$_2$ in water;
   (b) contacting the partially wet carrier with a powder of the iron phosphorus oxide catalyst to form a mixture;
   (c) agitating said mixture to form the coated catalyst;
   (d) drying said coated catalyst;
   (e) calcining said coated catalyst.

18. A catalyst as in claim 17, wherein said carrier is selected from the group silica, alumina, alumina-silica, silicon carbide, titania and zirconia.

19. A catalyst as in claim 17, wherein said iron phosphorus oxide catalyst has the empirical formula $$A_aFe_bP_cD_dO_x$$

wherein
A selected from the group Al, B, Be, Cd, Co, Cr, Ga, Ge, In, Ni, Te, Th, Ti, Tl, U, V, Zn, Zr, rare earths and mixtures thereof,
wherein
D is selected from the group Ag, Cu, Mn and mixtures thereof,
and wherein
a=0-1
b=0.75-1.5
c=1-2
d=0-2
a+d is greater than zero and
x is the number of oxygens needed to satisfy the valence requirements of the remaining elements.

* * * * *